United States Patent [19]
Kiefer et al.

[11] 4,032,235
[45] June 28, 1977

[54] APPARATUS FOR BACKGROUND ABSORPTION COMPENSATION IN SPECTROPHOTOMETERS

[75] Inventors: Hans Walter Kiefer, Nussdorf; Lothar Herbert Riethmüller, Uhldingen-Muhlhofen; Ernst Günther Robert Spreitzhofer, Nussdorf, all of Germany

[73] Assignee: The Perkin-Elmer Corporation, Norwalk, China /Taiwan

[22] Filed: Nov. 24, 1975

[21] Appl. No.: 634,928

[30] Foreign Application Priority Data
Nov. 30, 1974 Germany .......................... 2456713

[52] U.S. Cl. .................................. 356/82; 356/93; 356/95; 356/97
[51] Int. Cl.² ........................ G01J 3/36; G01J 3/42
[58] Field of Search .................. 356/82, 88, 93, 95, 356/97

[56] References Cited
UNITED STATES PATENTS
3,901,601  8/1975  Lahmann ............................ 356/97

*Primary Examiner*—Vincent P. McGraw
*Attorney, Agent, or Firm*—S. A. Giarratana; F. L. Masselle; J. M. O'Meara

[57] ABSTRACT

The photoelectric detector output in the spectrophotometer is amplified with separate stages of fixed and variable gain to derive background absorption compensation when the intensity of the continuous spectrum emitting radiation source therein varies from optimum levels. Where a reference output of the photoelectric detector is desirable for the background absorption compensation, a dark interval of the photoelectric detector and an output channel are provided for each gain stage.

10 Claims, 5 Drawing Figures

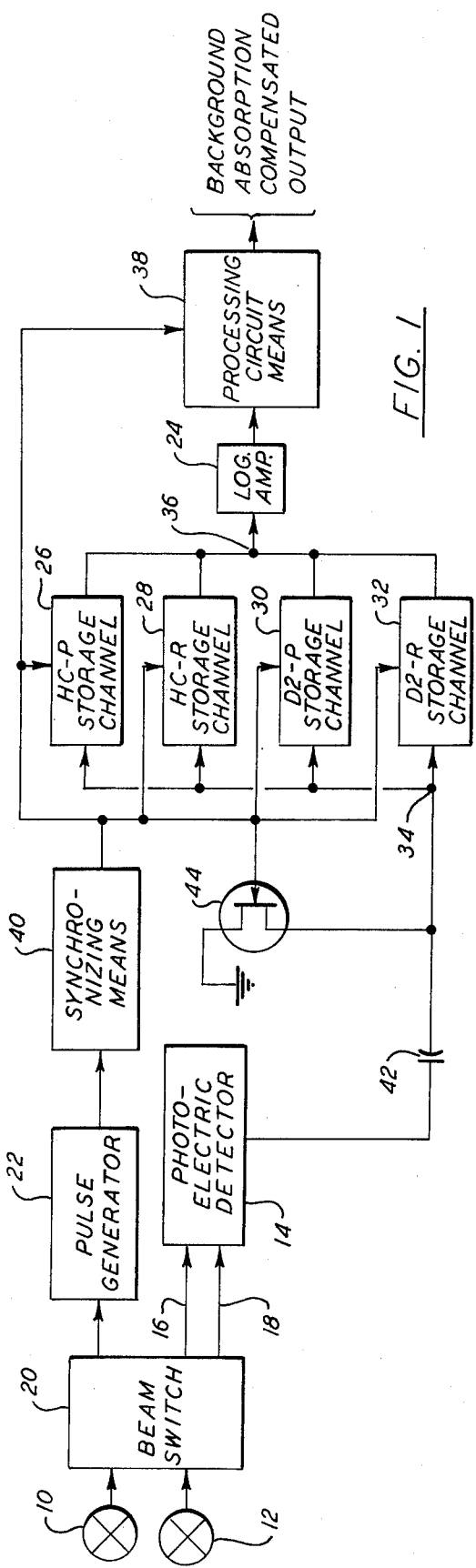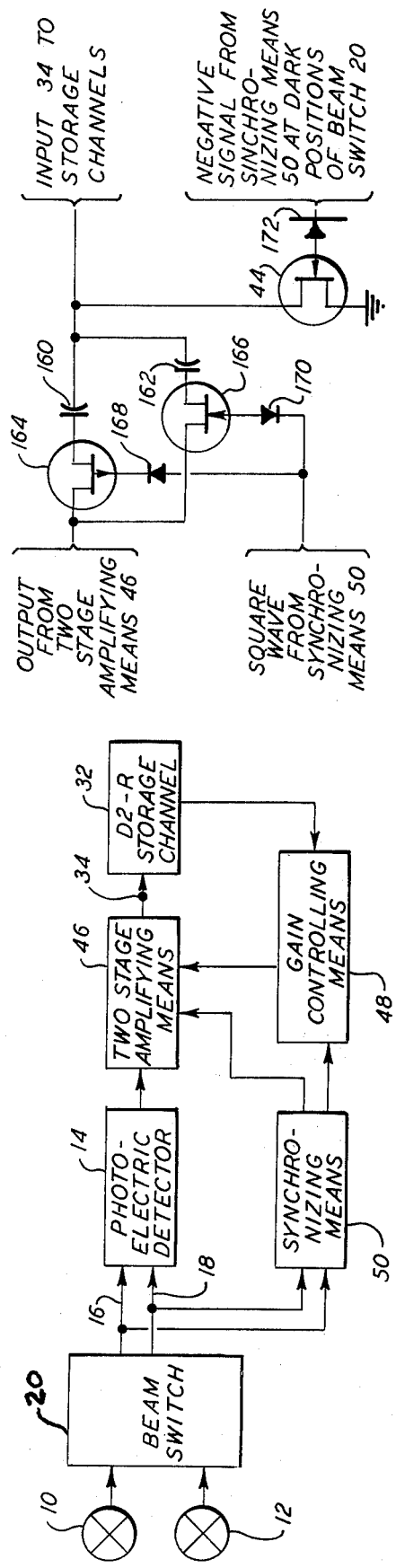

APPARATUS FOR BACKGROUND ABSORPTION COMPENSATION IN SPECTROPHOTOMETERS

BACKGROUND OF THE INVENTION

The present invention relates to apparatus for deriving valid background absorption compensation in a spectrophotometer when the intensity of the continuous spectrum emitting radiation source therein varies beyond optimum levels. It is commonly known in the art that readouts of spectrophotometers can be compensated for background absorption if radiant energy sources for emitting a resonance line of the sample being evaluated and a continuous spectrum containing the resonance line are included therein. Of course, the prior art for such compensation is predicated on the assumption that the background absorption of the continuous spectrum emitting radiation source is the same for all wavelengths in the spectrum thereof and at any intensity of that source. However, this assumption is not strictly valid and as the intensity of the continuous spectrum emitting radiation source varies over wider ranges, the background absorption compensation derived therewith becomes less accurate.

SUMMARY OF THE INVENTION

It is the general object of the present invention to provide a spectrophotometer having background absorption compensation which overcomes or mitigates the disadvantages of the prior art.

It is a specific object of the present invention to provide a spectrophotometer which is compensated for background absorption even though the intensity of the continuous spectrum emitting radiation source therein varies over such a range that significantly inaccurate compensation would otherwise result.

It is another object of the present invention to provide the background absorption compensation thereof from photoelectric detector outputs having reference levels that are predicated on dark intervals of the photoelectric detector.

These objects are accomplished according to the concept of the present invention by amplifying the photoelectric detector output of the spectrophotometer in separate stages of fixed and variable gain respectively, while radiant energy is directed to the photoelectric detector from a resonance line emitting radiation source during a first interval and from a continuous spectrum emitting radiation source during a second interval. The variable gain is controlled in proportion to the intensity of the continuous spectrum emitting radiation source throughout the second interval, while both gain stages and the variable gain control are synchronized with the sequence at which the radiation sources are directed to the photoelectric detector. Parallel output channels to a grounding switch and each having a capacitor therein, are utilized where desirable to derive the background absorption compensation relative to dark interval outputs of the photoelectric detector.

BRIEF DESCRIPTION OF THE DRAWINGS

The manner in which these and other objects of the present invention are achieved will be best understood by reference to the following description, the appended claims, and the attached drawings wherein:

FIG. 1 is a circuit block diagram of a spectrophotometer arrangement by which readouts thereof are compensated for background absorption;

FIG. 2 is a modified portion of FIG. 1 with the block diagram of the present invention incorporated therein;

FIG. 5 is the circuit diagram for one embodiment of the output channels which can be incorporated with this invention to derive the background absorption compensation relative to dark interval outputs from the photoelectric detector of the spectrophotometer.

DESCRIPTION OF THE PREFERRED EMBODIMENTS

Figure 3:
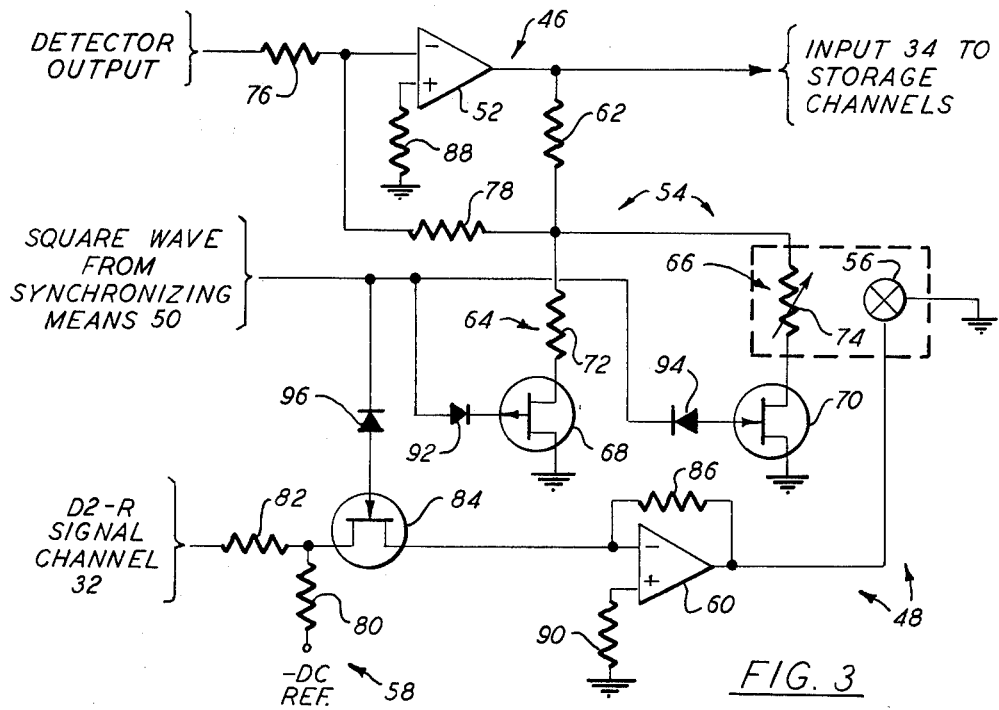
FIG. 3 is an analog circuit diagram for one embodiment of this invention.

Turning now to the drawings, one spectrophotometer arrangement for producing a readout which is compensated for background absorption is illustrated in FIG. 1. Radiant energy from a first source 10 and a second source 12 are each successively directed to a photoelectric detector 14 along both a sample path 16 and a reference path 18 by a beam switch 20 which continuously cycles through a sequence of positions. The beam switch 20 is connected with a generator means 22 for producing a pulse at each position thereof, while output from the photoelectric detector 14 is connected to a logarithmic amplifier 24 through four storage channels 26, 28, 30 and 32 which all have a common input 34. The logarithmic amplifier 24 is connected between a common output 36 from the storage channels 26, 28, 30 and 32 and a circuit means 38 for mathematically processing the logarithmic outputs to the desired compensated readout. Each of the storage channels 26, 28, 30 and 32 includes input and output switches (not shown) which are controlled along with the processing circuit means 38, by means 40 for synchronizing the output of the photoelectric detector 14 with the pulses of the generator means 22. Although those skilled in the art of spectrophotometry will understand the functional aspects of the processing circuit means 38 without further explanation, the general nature thereof is explained in U.S. Pat. No. 3,901,601 which has been assigned to the same assignee as this application. Otherwise, circuit details as to the spectrophotometer arrangement of FIG. 1 are disclosed in pending application Ser. No. 549,157 filed on Feb. 12, 1975 Pat. No. 3,967,900, and assigned to the same assignee as this application.

Actually, the first and second sources 10 and 12 are respectively of the type which emit a resonance line for the sample being evaluated, such as a hollow cathode (HC) lamp, and a continuous spectrum containing the resonance line, such as a deuterium (D2) lamp. When the HC and D2 lamps are utilized, the processing circuit means 38 derives the compensated readout of the spectrophotometer in accordance with the following mathematical expression:

$$-\log \frac{I_{HC-P} \times I_{D2-R}}{I_{HC-R} \times I_{D2-P}}$$

wherein, $I_{HC-P}$ is equal to the intensity of light from the hollow cathode lamp along the sample path and the photoelectric detector output thereof passes through storage channel 26;

$I_{HC-R}$ is equal to the intensity of light from the hollow cathode lamp along the reference path and the photoelectric detector output thereof passes through storage channel 28;

$I_{D2-P}$ is equal to the intensity of light from the deuterium lamp along the sample path and the photoelectric detector output thereof passes through storage channel 30; and $I_{D2-R}$ is equal to the intensity of light from the deuterium lamp along the reference path and the photoelectric detector output thereof passes through storage channel 32.

Therefore, a minimum of four positions would be included on the beam switch 20 in the spectrophotometer arrangement of FIG. 1. For applications where it is desirable to derive the background absorption compensation relative to dark interval outputs of the photoelectric detector 14, at least one position would be added to the beam switch 20 at which no energy from either the first or second sources 10 and 12 would be directed to either the sample or reference paths 16 and 18. Furthermore, in such applications, a capacitor 42 would be disposed between the photoelectric detector output and the common input 34 while an FET switch 44 would be disposed to ground the common input 34 throughout the dark intervals. Otherwise, any convenient method could be utilized to link the beam switch 20 with the pulse generator means 22, such as a slip ring commutating arrangement or a light pulse for each beam switch position. Of course, the background absorption compensation derived for the spectrophotometer arrangement of FIG. 1 is only valid if the intensity of the second source 12 remains within an optimum range and it is to this limitation that the concept of this invention is directed.

Generally, the concept of this invention is that any time energy from the second source 12 is directed to the photoelectric detector 14 by the beam switch 20, the output of the photoelectric detector 14 will be amplified at a gain which is controlled to provide an output as if the second source 12 were of optimum intensity. In FIG. 2, this concept is incorporated into the spectrophotometer arrangement of FIG. 1 by disposing a means 46 for amplifying in either a fixed gain stage or a variable gain stage between the photoelectric detector output and the common storage channel input 34. The D2-R signal from storage channel 32 is fed back to the amplifying means 46 through a means 48 for controlling the variable gain thereof in proportion to the intensity of the second source 12. Of course, the gain controlling means 48 includes a reference level that sets the optimum D2-R signal level at which background absorption compensation is provided and whenever the D2-R signal varies from this optimum, the variable gain of the amplifying means 46 adjusts to drive that signal back to the reference level. Otherwise, a means 50 for synchronizing the gain stages of the amplifying means 46 and the gain controlling means 48 with the position of the beam switch 20 is connected therebetween. The synchronizing means 50 programs the fixed gain stage to occur over a first interval while energy from the first source 10 (the HC lamp) is directed to the photoelectric detector 14 and programs the variable gain stage to occur over a second interval while energy from the second source (the D2 lamp) is directed to the photoelectric detector 14. Therefore, the fixed gain of the amplifying means 46 is preset to affect the photoelectric detector output 14 throughout the first interval in accordance with the conventional requirements of the spectrophotometer, while the variable gain thereof is continually controlled so that the effective photoelectric detector output throughout the second interval is as if the second source 12 were of optimum intensity.

Certainly, the synchronizing means 50 in this invention could be driven by the pulse generator 22 of FIG. 1 and, therefore, could be incoporated as part of the synchronizing means 40 in that figure. Otherwise, many circuit arrangements could be utilized in the invention for both the amplifying means 46 and the gain controlling means 48. One such circuit arrangement is illustrated in FIG. 3 where the amplifying means 46 includes an operational amplifier 52 with the output thereof connected to the inverting input thereof through a voltage dividing network 54 and where the gain controlling means 48 regulates the intensity of a third radiation source 56 in proportion to the difference between the intensity of the second source 12 and a reference level 58 through another operational amplifier 60. The voltage dividing network 54 includes a first fixed resistor 62 series connected to ground through two parallel legs 64 and 66 which each have an FET switch 68 and 70 connected respectively therein to a second fixed resistor 72 and a photoresistor 74. The photoelectric detector output is also connected to the inverting input of operational amplifier 52 through resistor 76, while the negative feedback thereof is taken from between the first fixed resistor 62 and the parallel legs 64 and 66 through resistor 78. A negative voltage as the reference level 58 and the D2-R signal from storage channel 32 which is proportional to the intensity of the second source 12 are connected in parallel through resistors 80 and 82 respectively, to the inverting input of operational amplifier 60 through FET switch 84. Output from operational amplifier 60 is also fed back through resistor 86 to the inverting input thereof and a capacitor (not shown) could be disposed in this feedback path to provide a proportional integrating characteristic. The noninverting inputs of operational amplifiers 52 and 60 are grounded in a conventional manner through resistors 88 and 90 respectively. The photoresistor 74 is illuminated by the third source 56 and the synchronizing means 50 applies a square wave having a positive excursion during the first interval and a negative excursion during the second interval through diodes 92, 94 and 96 to the gates of FET switches 68, 70 and 84. Switch 68 is conductive when a positive signal is applied to the gate thereof while switches 70 and 84 are conductive when negative signals are applied to the gates thereof and therefore, the diodes 92, 94 and 96 are disposed with the appropriate polarity to pass such signals.

Of course, the gain of any feedback amplifier depends on the nature of the feedback voltage which in FIG. 3 is derived from the voltage dividing network 54. During the first interval, the positive excursion of the square wave from the synchronizing means 50 is applied to the diodes 92, 94 and 96 with only FET switch 68 becoming conductive as a result thereof. Of course, the voltage dividing network 54 then includes fixed resistors 62 and 72, so that the amplifying means 46 will have a fixed gain. During the second interval, the negative excursion of the square wave from the synchronizing means 50 is applied to the diodes 92, 94 and 96 with FET switches 70 and 84 becoming conductive as a result thereof. Of course, the voltage dividing network 54 then includes the fixed resistor 62 and the photoresistor 74, so that the amplifying means 46 will have a variable gain depending on the resistance of the photoresistor 74. Because the third source 56 illuminates the photoresistor 74, the intensity of the former controls the resistance of the latter. Furthermore, the intensity of the third source 56 is conrolled in proportion to the difference between the D2-R signal and the reference level 58 by the operational amplifier 60. Therefore, the gain is fixed throughout the first interval while energy from the first source 10 is directed to the photoelectric detector 14 and the gain is varied so that the D2-R signal is controlled to the reference level 58 throughout the second interval while energy from the second source 12 is directed to the photoelectric detector 14.

Figure 4:
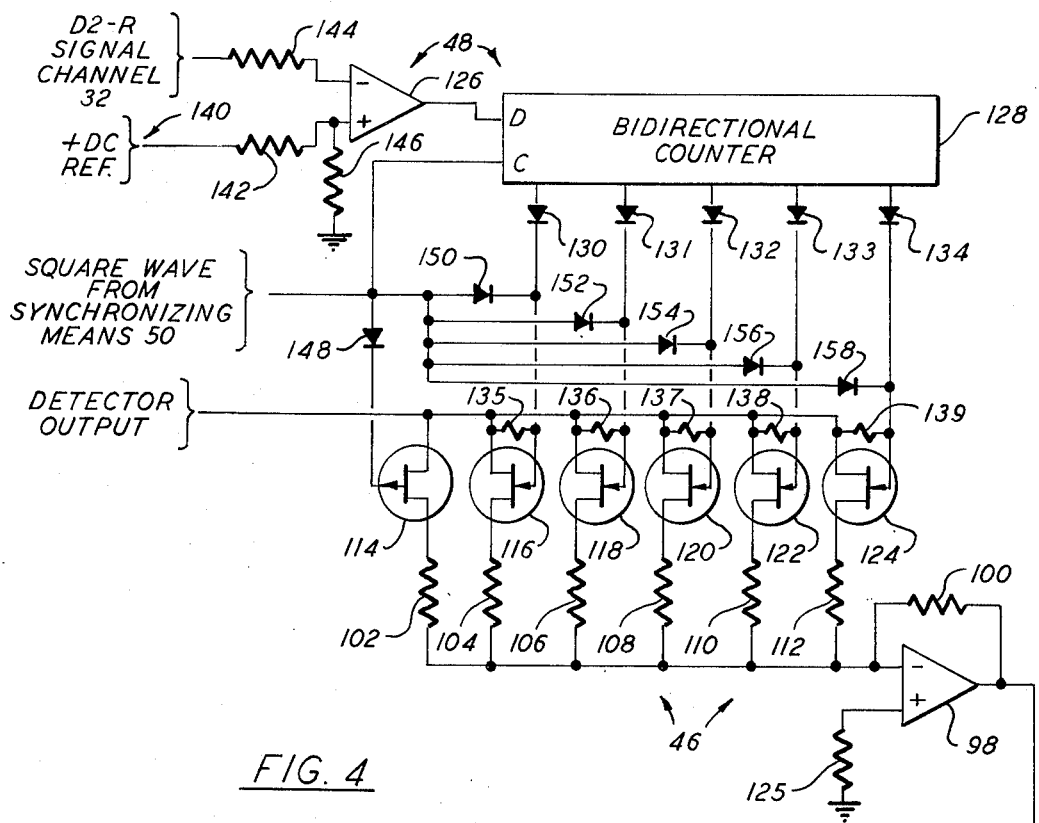
FIG. 4 is a digital circuit block diagram for another embodiment of this invention.

Another circuit arrangement for the amplifying means 46 and the gain controlling means 48 of this invention is illustrated in FIG. 4. For this arrangement, the amplifying means 46 includes an operational amplifier 98 with the inverting input thereof connected to both the output thereof through feedback resistor 100 and the photoelectric detector output through a plurality of resistors 102, 104, 106, 108, 110 and 112 having sequential values. The sequential resistors 102 through 112 are each series connected to an FET switch 114, 116, 118, 120, 122 and 124 respectively, in parallel legs and the noninverting input of operational amplifier 98 is grounded through resistor 125. The gain controlling means 48 includes an operational amplifier 126 connected as a comparator and a bi-directional counter 128 having the negative count outputs thereof individually connected through diodes 130, 131, 132, 133 and 134 respectively, to the gates of all the switches in the parallel legs except switch 114. The detector output is conditioned to appear as a negative excursion during at least the second interval and the gates of switches 116 through 124 are connected to the detector output through resistors 135, 136, 137, 138 and 139 respectively. A positive voltage as a refference level 140 and the D2-R signal from storage channel 32 which is proportional to the intensity of the second source 12, are connected respectively through resistors 142 and 144 to the inverting and noninverting inputs of the operational amplifier 126. The noninverting input of operational amplifier 126 is also grounded through resistor 146 and the output therefrom is connected to the count direction input D of the bi-directional counter 128. The synchronizing means 50 again applies a square wave having a positive excursion throughout the first interval and a negative excursion throughout the second interval to the clock input C of the bi-directional counter 128 and to the gates of all the switches 114 through 124 via diodes 148, 150, 152, 154, 156 and 158 respectively. Switch 114 is conductive when a positive signal is applied to the gate thereof, while switches 116, 118, 120, 122 and 124 are conductive when a negative signal is applied to the gates thereof and the diodes 148 through 158 are disposed to pass the positive excursions of the square wave from the synchronizing means 50, while the diodes 130 through 134 are disposed to pass positive signals from the count outputs of the bi-directional counter 128.

Since operational amplifier 98 is connected in what is commonly known as an inverting configuration, the gain of the amplifying means 46 of FIG. 4 is equal to the feedback resistance over the input resistance. During the first interval, the positive excursion of the square wave from the synchronizing means 50 is applied to the diodes 148 through 158 with only FET switch 114 becoming conductive as a result thereof. Of course, the input resistance of the amplifying means 46 is then equal to the value of resistor 102 and the gain thereof will be fixed in accordance with this value. Otherwise, the positive excursion of the square wave holds the switches 116 through 124 in the nonconductive state, regardless of which negative count output is presented by the bidirectional counter 128. During the second interval, the negative excursion of the square wave from the synchronizing means 50 causes switch 114 to be nonconductive, but it is blocked from switches 116 through 124 by diodes 150 through 158 respectively. However, the negative excursion of the detector output during the second interval causes the switches 116 through 124 which do not receive positive gate signals from the bi-directional counter 128 via diodes 130 through 134, to be conductive via resistors 135 through 139. During the second interval therefore, one of the switches 116 through 124 will become conductive depending on which count output is presented by the bi-directional counter 128. Of course, only one of the resistors 104 through 112 will then be the input resistance of the amplifying means 46 and the gain thereof will be varied in accordance with the value of that resistor throughout the second interval. The bi-directional counter 128 receives one clock input for each square wave cycle from the synchronizing means 50 but only receives a count direction input from the comparator when a difference exists between the D2-R signal and the reference level 140. Of course, when a clock input and a count direction input are received simultaneously, the bi-directional counter 128 steps to the next count output thereof in the direction determined by the polarity of the difference existing between the D2-R signal and the reference level 140. Therefore, the gain is fixed throughout the first interval while energy from the first source 10 is directed to photoelectric detector 14 and the gain is varied throughout the second interval while energy from the second source 12 is directed to the photoelectric detector 14 in accordance with the cumulative number of clock inputs and count direction inputs having either polarity that are simultaneously received by the counter 128.

Of course, the capacitor 42 and the grounding switch 44 in the circuit block diagram of FIG. 1, as well as the dark positions on the beam switch 20 which were discussed previously, could be incorporated with the background absorption compensation circuitry of this invention. However, because of the distinct first and second intervals over which the gain of the amplifying means 46 is fixed and variable respectively, at least two output channels should be utilized to direct output from the amplifying means 46 to the storage channels 26 through 32. As shown in FIG. 5, each of the output channels would include a capacitor 160 and 162 respectively connected in series with a FET switch 164 and 166 respectively. Of course, FET switch 44 continues to be connected between ground and the common input 34 to the storage channels in FIG. 5. The positive and negative excursions of the square wave from the synchronizing means 50 are applied to the gates of switches 164 and 166 through diodes 168 and 170 respectively. Switches 164 and 166 are conductive when positive and negative signals respectively are applied to the gates thereof and the diodes 168 and 170 are disposed in the circuit with the appropriate polarity to pass such signals. Furthermore, at each dark position of the beam switch 20, the synchronizing means 50 applies a negative signal through diode 172 to the gate of switch 44 and thereby renders that switch conductive. Of course, this negative signal is analogous to that available at the collector of transistor 218 in FIG. 1A of the previously mentioned copending application Ser. No. 549,157 which was filed on Feb. 12, 1975 U.S. Pat. No. 3,967,900.

What we claim is:

1. In a spectrophotometer of the type wherein readouts compensated for background absorption are provided by sequentially directing radiant energy from each of first and second sources along sample and reference paths to a photoelectric detector, the improvement comprising:
    means for amplifying the photoelectric detector output in separate stages at either a fixed gain or a variable gain;
    means for controlling said variable gain of said amplifying means in proportion to the intensity variation of the second source from an optimum level; and
    means for synchronizing said stages of said amplifying means and said gain controlling means so that the fixed gain stage occurs over a first interval while energy from the first source is directed to the photoelectric detector and the variable gain stage occurs over a second interval while energy from the second source is directed to the photoelectric detector.

2. The combination of claim 1 wherein said amplifying means includes an operational amplifier with the output thereof connected to the inverting input thereof through a voltage dividing network; and wherein said gain controlling means regulates the intensity of a third radiant energy source in proportion to the difference between the intensity of the second source and a reference level, said voltage dividing network being a first fixed resistor series connected to ground through two parallel legs, each said leg having a staging switch series connected therein to a second fixed resistor and a photoresistor respectively, said photoresistor being illuminated from said third source and said synchronizing means rendering said staging switches alternately conductive throughout said first and second intervals respectively.

3. The combination of claim 1 wherein said amplifying means includes an operational amplifier with the inverting input thereof jointly connected to the output thereof through a feedback resistor and to the photoelectric detector output through a plurality of input resistors in parallel legs, said input resistors being of sequential values and having a switch series connected thereto in each said parallel leg; and wherein said gain controlling means includes a bidirectional counter with the count outputs thereof individually connected to render said switches in said parallel legs conductive except for an initial switch therein, said bidirectional counter having the count direction input thereof connected to a signal relating to the differential between the intensity of the second source and a reference level, said synchronizing means rendering said initial switch conductive throughout said first interval and supplying a pulse to the clock input of said bidirectional counter during each cycle of said first and second intervals, the count output from said bidirectional counter being proportional to the number of said cycles during which the intensity of the second source differed from said reference level in either direction of polarity.

4. The combination of claim 1 wherein said synchronizing means includes a continuously cycling beam switch having a first position at which energy from the first source is directed along the reference path, a second position at which energy from the first source is directed along the sample path, a third position at which energy from the second source is directed along the sample path, and a fourth position at which energy from the second source is directed along the reference path; and wherein said first interval occurs throughout the first and second positions of each beam switch cycle while said second interval occurs throughout the third and fourth positions of each beam switch cycle.

5. The combination of claim 1 wherein said synchronizing means includes a continuously cycling beam switch having a first position at which no energy from either source is directed along either the sample or reference paths, a second position at which energy from the first source is directed along the reference path, a third position at which energy from the first source is directed along the sample path, a fourth position at which no energy from either source is directed along either the sample or reference paths, a fifth position at which energy from the second source is directed along the sample path, and a sixth position at which energy is directed from the second source along the reference path; and wherein said first interval occurs throughout the first, second and third positions of each beam switch cycle while said second interval occurs throughout the fourth, fifth, and sixth positions of each beam switch cycle.

6. The combination of claim 5 wherein output from said amplifying means is directed through a pair of parallel channels to a common output terminal, each said output channel having a switch and a capacitor series connected therein, said common output terminal being grounded through a switch, said synchronizing means rendering said output channel switches alternately conductive throughout said first and second intervals respectively and rendering said grounding switch conductive at the first and fourth positions of each beam switch cycle.

7. The combination of claim 5 wherein said amplifying means includes an operational amplifier with the output thereof connected to the inverting input thereof through a voltage dividing network; and wherein said gain controlling means regulates the intensity of a third radiant energy source in proportion to the difference between the intensity of the second source and a reference level, said voltage dividing network being a first fixed resistor series connected to ground through two parallel legs, each said leg having a staging switch series connected therein to a second fixed resistor and a photoresistor respectively, said photoresistor being illuminated from said third source and said synchronizing means rendering said staging switches alternately conductive throughout said first and second intervals respectively.

8. The combination of claim 7 wherein output from said amplifying means is directed through a pair of parallel channels to a common output terminal, each said output channel having a switch and a capacitor series connected therein, said common output terminal being grounded through a switch, said synchronizing means rendering said output channel switches alternately conductive throughout said first and second intervals respectively and rendering said grounding switch conductive at the first and fourth positions of each beam switch cycle.

9. The combination of claim 5 wherein said amplifying means includes an operational amplifier with the inverting input thereof jointly connected to the output thereof through a feedback resistor and to the photoelectric detector output through a plurality of input resistors in parallel legs, said input resistors being of sequential values and having a switch series connected thereto in each said parallel leg; and wherein said gain controlling means includes a bidirectional counter with the count outputs thereof individually connected to render said switches in said parallel legs conductive except for an initial switch therein, said bidirectional counter having the count direction input thereof connected to a signal relating to the differential between the intensity of the second source and a reference level, said synchronizing means rendering said initial switch conductive throughout said first interval and supplying a pulse to the clock input of said bidirectional counter during each cycle of said first and second intervals, the count output from said bidirectional counter being proportional to the number of said cycles during which the intensity of the second source differed from said reference level in either direction of polarity.

10. The combination of claim 9 wherein output from said amplifying means is directed through a pair of parallel channels to a common output terminal, each said output channel having a switch and a capacitor series connected therein, said common output terminal being grounded through a switch, said synchronizing means rendering said output channel switches alternately conductive throughout said first and second intervals respectively and rendering said grounding switch conductive at the first and fourth positions of each beam switch cycle.

* * * * *

UNITED STATES PATENT AND TRADEMARK OFFICE
CERTIFICATE OF CORRECTION

PATENT NO. : 4,032,235

DATED : June 28, 1977

INVENTOR(S) : Hans Walter Kiefer et al

It is certified that error appears in the above–identified patent and that said Letters Patent are hereby corrected as shown below:

On the front page of the patent, please correct the address of the assignee from "Norwalk, China/Taiwan" to --Norwalk, Connecticut--.

*Signed and Sealed this*

*Fourth* Day of *October 1977*

[SEAL]

Attest:

RUTH C. MASON
*Attesting Officer*

LUTRELLE F. PARKER
*Acting Commissioner of Patents and Trademarks*